US00PP30517P3

(12) United States Plant Patent
Kerley et al.

(10) Patent No.: US PP30,517 P3
(45) Date of Patent: May 21, 2019

(54) ***CALENDULA* PLANT NAMED 'KERCALDIVA'**

(50) Latin Name: *Calendula hybrida*
Varietal Denomination: Kercaldiva

(71) Applicants: Timothy Edward Kerley, Willingham (GB); Sarah Elisabeth Kerley, Willingham (GB); David William Kerley, Over (GB); Priscilla Grace Kerley, Over (GB)

(72) Inventors: Timothy Edward Kerley, Willingham (GB); Sarah Elisabeth Kerley, Willingham (GB); David William Kerley, Over (GB); Priscilla Grace Kerley, Over (GB)

( * ) Notice: Subject to any disclaimer, the term of this patent is extended or adjusted under 35 U.S.C. 154(b) by 0 days.

(21) Appl. No.: 15/732,080

(22) Filed: Sep. 14, 2017

(65) Prior Publication Data

US 2019/0082575 P1 Mar. 14, 2019

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02; A01H 6/14
See application file for complete search history.

(56) References Cited

PUBLICATIONS

Pollinator Gardens 2017, Burlington Waterfront Display Gardens, retrieved on Aug. 7, 2018, retrieved from Internet at https://pollinatorgardens.org/2017/06/27/waterfront2017/, pp. 1-5. (Year: 2017).*

Proven Winners 2018, Lady Godiva Orange English Marigold *Calendula* hybrid, retrieved on Aug. 7, 2018, retrieved from the Internet at https://www.provenwinners.com/plants/calendula/lady-godiva-orange-english-marigold-calendula-hybrid, pp. 1-3. (Year: 2018).*

* cited by examiner

*Primary Examiner* — June Hwu
(74) *Attorney, Agent, or Firm* — C. A. Whealy

(57) ABSTRACT

A new and distinct cultivar of *Calendula* plant named 'Kercaldiva', characterized by its compact, upright to outwardly spreading and mounding plant habit; moderately vigorous growth habit; freely branching habit; dense and bushy appearance; freely and continuously flowering habit; long flowering period; large double and semi-double type inflorescences with bright orange-colored ray florets; and good container and landscape performance.

3 Drawing Sheets

Botanical designation: *Calendula hybrida*.
Cultivar denomination: 'KERCALDIVA'.

BACKGROUND OF THE INVENTION

The present invention relates to a new and distinct cultivar of *Calendula* plant, botanically known as *Calendula hybrida* and hereinafter referred to by the name 'Kercaldiva'.

The new *Calendula* plant is a product of a planned breeding program conducted by the Inventors in Cambridge, United Kingdom. The objective of the breeding program is to create new uniform *Calendula* plants that flower continuously for a long period of time and have good container and landscape performance.

The new *Calendula* plant originated from a cross-pollination of a proprietary selection of *Calendula hybrida* identified as code number 11-67-5, not patented, as the female, or seed, parent with a proprietary selection of *Calendula hybrida* identified as code number 11-67-8, not patented, as the male, or pollen, parent in 2011. The new *Calendula* plant was discovered and selected by the Inventors as a single flowering plant from within the progeny of the stated cross-pollination in a controlled greenhouse environment in Cambridge, United Kingdom in July, 2012.

Asexual reproduction of the new *Calendula* plant by vegetative tip cuttings in a controlled greenhouse environment in Cambridge, United Kingdom since August, 2012 has shown that the unique features of this new *Calendula* plant are stable and reproduced true to type in successive generations.

SUMMARY OF THE INVENTION

Plants of the new *Calendula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Calendula*. These characteristics in combination distinguish 'Kercaldiva' as a new and distinct *Calendula* plant:

1. Compact, upright to outwardly spreading and mounding plant habit.
2. Moderately vigorous growth habit.
3. Freely branching habit; dense and bushy appearance.
4. Freely and continuously flowering habit
5. Long flowering period.
6. Large double and semi-double type inflorescences with bright orange-colored ray florets.
7. Good container and landscape performance.

Plants of the new *Calendula* differ primarily from plants of the female parent selection in inflorescence form as plants of the female parent selection have single-type inflorescences.

Plants of the new *Calendula* differ primarily from plants of the male parent selection in the following characteristics:

1. Plants of the new *Calendula* are more freely branching than plants of the male parent selection.
2. Plants of the new *Calendula* and the male parent selection differ in inflorescence form as plants of the male parent selection have single-type inflorescences.
3. Ray florets of plants of the new *Calendula* resist fading whereas ray florets of plants of the male parent selection fade to yellow with development.

Plants of the new *Calendula* can be compared to plants of *Calendula officinalis* 'Cheers Orange', not patented. In side-by-side comparisons, plants of the new *Calendula* differ primarily from plants of 'Cheers Orange' in the following characteristics:

1. Plants of the new *Calendula* are more outwardly spreading than and not as upright as plants of 'Cheers Orange'.
2. Plants of the new *Calendula* have larger inflorescences than plants of 'Cheers Orange'.
3. Plants of the new *Calendula* and 'Cheers Orange' differ in inflorescence form as plants of 'Cheers Orange' have semi-double and single-type inflorescences.
4. Ray florets of plants of the new *Calendula* are darker orange in color than ray florets of plants of 'Cheers Orange'.

Plants of the new *Calendula* also can be compared to plants of *Calendula officinalis* '20123-107D', disclosed in U.S. Plant Pat. No. 26,804. In side-by-side comparisons, plants of the new *Calendula* differ primarily from plants of '20123-107D' in the following characteristics:

1. Plants of the new *Calendula* are more freely branching than plants of '20123-107D'.
2. Plants of the new *Calendula* have shorter leaves than plants of '20123-107D'.
3. Plants of the new *Calendula* are more freely flowering than plants of '20123-107D'.
4. Plants of the new *Calendula* are more tolerant to Powdery Mildew than plants of '20123-107D'.

BRIEF DESCRIPTION OF THE PHOTOGRAPHS

The accompanying photographs illustrate the overall appearance of the new *Calendula* plant showing the colors as true as it is reasonably possible to obtain in colored reproductions of this type. Colors in the photographs may differ slightly from the color values cited in the detailed botanical description which accurately describe the colors of the new *Calendula* plant.

The photograph on the first sheet is a side perspective view of a typical flowering plant of 'Kercaldiva' grown in a container.

The photograph on the second sheet is a close-up view of a typical flowering plant of 'Kercaldiva'.

The photograph on the third sheet is a side-by-side perspective view of a typical flowering plant of 'Kercaldiva' (left) and a typical flowering plant of 'Cheers Orange' (right).

DETAILED BOTANICAL DESCRIPTION

The aforementioned photographs and following observations and measurements describe plants grown during the spring in 11.5-liter containers in a glass-covered greenhouse in Cambridge, United Kingdom and under cultural practices typical of commercial *Calendula* production. Plants were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calendula hybrida* 'Kercaldiva'.

Parentage:

*Female, or seed, parent*.—Proprietary selection of *Calendula hybrida* identified as code number 11-67-5, not patented.

*Male, or pollen, parent*.—Proprietary selection of *Calendula hybrida* identified as code number 11-67-8, not patented.

Propagation:

*Type*.—By vegetative tip cuttings.

*Time to initiate roots, summer*.—About seven days at soil temperatures about 21° C.

*Time to initiate roots, winter*.—About ten days at soil temperatures about 18° C.

*Time to produce a rooted young plant, summer*.—About three weeks at soil temperatures about 21° C.

*Time to produce a rooted young plant, winter*.—About four weeks at soil temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact, upright to somewhat outwardly spreading and mounding plant habit; moderately vigorous growth habit and moderate growth rate.

*Branching habit*.—Freely branching habit with about three to four main stems each main stem with about three to four lateral branches; dense and bushy appearance.

*Plant height*.—About 19 cm.

*Plant diameter or spread*.—About 31 cm.

*Lateral branches*.—Length: About 21 cm. Diameter: About 8 mm. Internode length: About 4 cm. Strength: Strong. Aspect: Main stems, mostly upright; lateral stems about 45° from main stems. Texture and luster: Slightly pubescent; matte. Color: Close to 146B to 146C.

Leaf description:

*Arrangement*.—Alternate, simple; sessile.

*Length*.—About 11 cm.

*Width*.—About 4.5 cm.

*Shape*.—Oblanceolate.

*Apex*.—Acute.

*Base*.—Truncate.

*Margin*.—Sinuate.

*Texture and luster, upper and lower surfaces*.—Smooth, glabrous; matte.

*Venation pattern*.—Pinnate.

*Color*.—Developing leaves, upper surface: Close to 146A. Developing leaves, lower surface: Close to 146B. Fully expanded leaves, upper surface: Close to 147A; venation, close to 146B. Fully expanded leaves, lower surface: Close to 147B; venation, close to 146C.

Inflorescence description:

*Appearance*.—Double and semi-double type inflorescences developing on terminal and axillary peduncles; double-type inflorescences with numerous ray florets and none to a few disc florets; semi-double type inflorescences with numerous ray florets and a significant number of disc florets; inflorescences positioned on moderately strong peduncles; inflorescences face mostly upright to outwardly.

*Flowering habit*.—Freely flowering habit numerous inflorescences develop during the flowering season; strongly floriferous.

*Fragrance*.—None detected.

*Flowering response*.—Early flowering habit, plants begin flowering about five weeks after planting.

*Natural flowering season*.—Long flowering period, plants flower continuously from spring until frost in temperate regions.

*Inflorescence longevity*.—Depending on actual temperature, inflorescences last about seven to ten days on the plant; inflorescences persistent.

*Inflorescence buds*.—Height: About 1.2 cm. Diameter: About 1.5 cm. Shape: Ovate. Texture and luster: Slightly pubescent; matte. Color: Close to 146A; distally, close to 24A and 172A.

*Inflorescence size*.—Diameter: About 7 cm. Height (depth): About 3 cm. Disc diameter (semi-double inflorescences): About 1 cm.

*Receptacles*.—Receptacle diameter: About 1.3 cm. Receptacle height: About 5 mm. Receptacle color: Close to 144B.

*Ray florets*.—Number of ray florets per inflorescence, double inflorescences: About 133 arranged in about six whorls. Number of ray florets per inflorescence, semi-double inflorescences: About 62 arranged in about three to four whorls. Length: About 3.1 cm. Width: About 5 mm. Shape: Oblanceolate. Apex: Praemorse. Base: Narrowly cuneate. Margin: Entire. Aspect: Mostly horizontal, apices weakly reflexing with development. Texture and luster, upper surface: Smooth, glabrous; glossy. Texture and luster, lower surface: Smooth, glabrous; matte. Color: When opening, upper surface: Close to 24A; at the apices, tinted with close to 172A. When opening, lower surface: Towards the apex, close to 23A, at the apices, overlain with close to 172B; towards the base, close to 12A. Fully opened, upper surface: Close to 24A; towards the base, tinted with close to 15A; venation, similar to lamina; color does not fade with development. Fully opened, lower surface: Towards the apex, close to 23A, at the apices, overlain with close to 172B; towards the base, close to 12B; color does not fade with development.

*Disc florets*.—Number of disc florets per inflorescence: Double-type inflorescences have none to about six; semi-double inflorescences have about 86 to 92 arranged in about five whorls at the center of the receptacle. Length: About 4 mm. Diameter: About 2 mm. Shape: Tubular, slender; apex, five-pointed. Texture and luster: Smooth, glabrous; matte. Color: Close to 178A.

*Phyllaries*.—Quantity per inflorescence and arrangement: About 23 arranged in two whorls. Length: About 1 cm. Width: About 2 mm. Shape: Narrowly deltoid. Apex: Acute. Base: Truncate. Margin: Entire. Aspect: When opening, mostly upright; open inflorescences, mostly horizontal. Texture and luster, upper surface: Slightly pubescent; glossy. Texture and luster, lower surface: Slightly pubescent; matte. Color, upper surface: Close to 146A. Color, lower surface: Close to 146A; at the apices, overlain with close to 178A.

*Peduncles*.—Length, terminal peduncle: About 2.2 cm. Diameter, terminal peduncle: About 3 mm. Strength: Moderately strong. Aspect: Initially upright, outwardly bending with development. Texture and luster: Slightly pubescent; matte. Color: Close to 144A.

*Reproductive organs*.—Androecium (present on disc florets only): Quantity per floret: Four. Filament length: About 1 mm. Filament color: Close to 164C. Anther shape: Lanceolate. Anther length: About 1 mm to 2 mm. Anther color: Close to 172D. Pollen amount: Moderate. Pollen color: Close to 26A. Gynoecium (present on ray and disc florets): Quantity per disc floret: One. Pistil length: About 4 mm. Style length: About 2 mm. Style color: Close to 15A. Stigma shape: Bi-parted. Stigma color: Close to 178A. Ovary color: Close to 144C.

*Seeds and fruits*.—Seed and fruit development have not been observed on plants of the new *Calendula* to date.

Disease & pest tolerance: Plants of the new *Calendula* have been observed to be somewhat tolerant to Powdery Mildew (*Golovinomyces cichoracearum*). Plants of the new *Calendula* have not been shown to be tolerant to pests and other pathogens common to *Calendula* plants.

Garden performance: Plants of the new *Calendula* have been observed to have good garden performance and to tolerate temperatures from about −5° C. to about 40° C. and are suitable for USDA Hardiness Zones 10 and 11.

It is claimed:

1. A new and distinct *Calendula* plant named 'Kercaldiva' as illustrated and described.

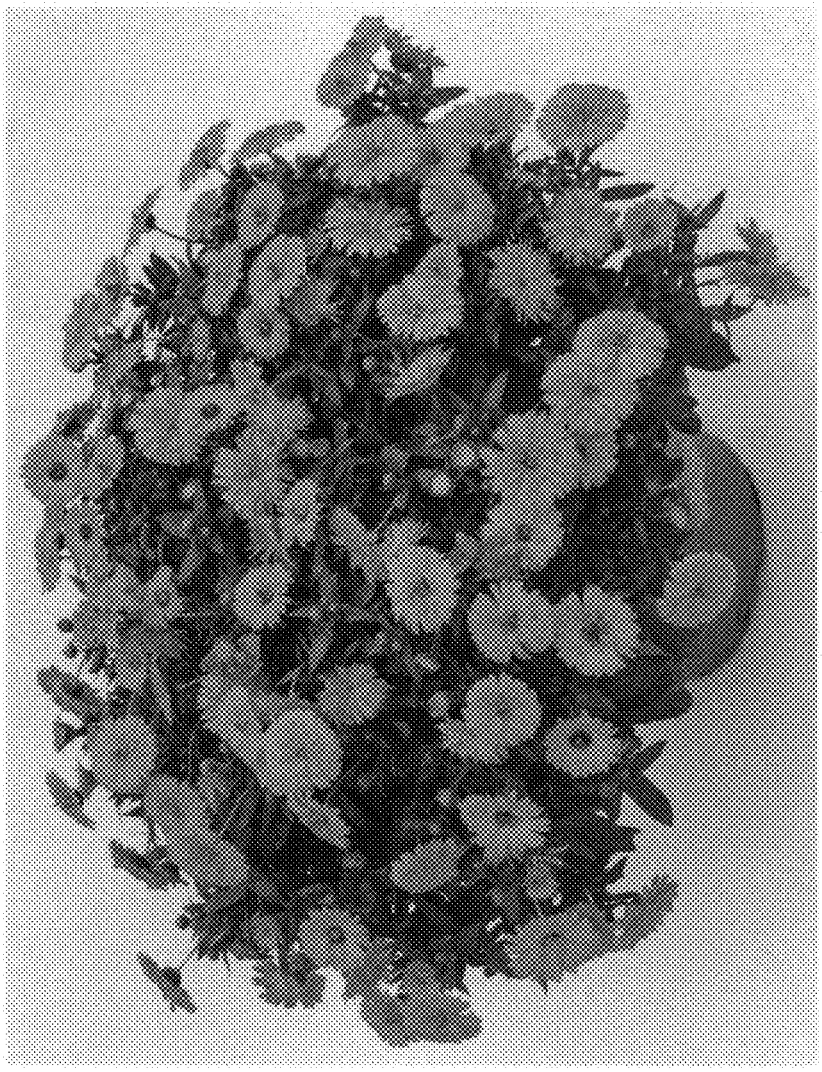

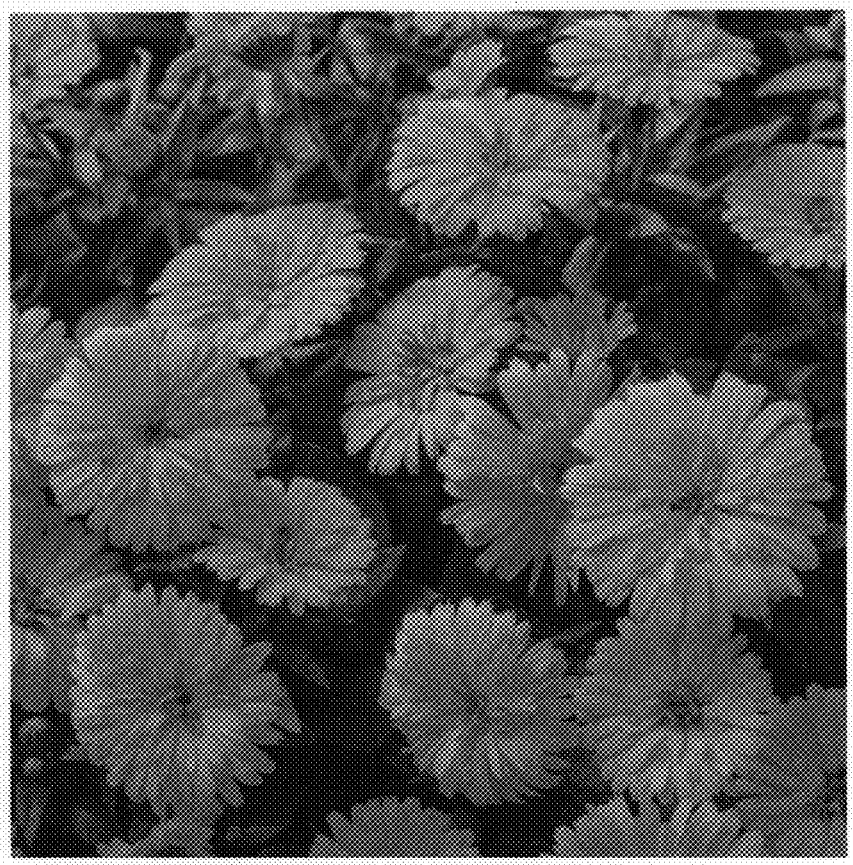

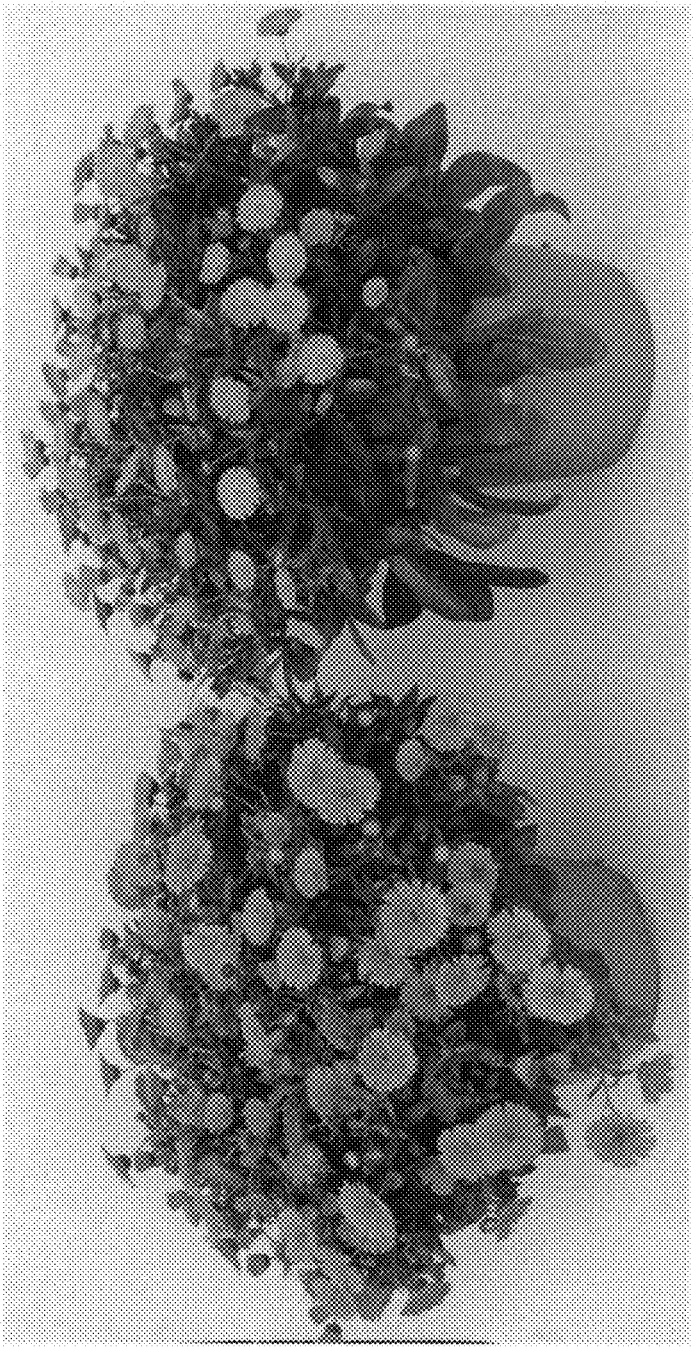

* * * * *